United States Patent [19]

Hunkeler et al.

[11] Patent Number: 4,616,010

[45] Date of Patent: Oct. 7, 1986

[54] IMIDAZODIAZEPINE DERIVATIVES

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 831,206

[22] Filed: Feb. 20, 1986

[30] Foreign Application Priority Data

Feb. 28, 1985 [CH] Switzerland .......................... 902/85

[51] Int. Cl.[4] .................... A61K 31/55; C07D 487/14; C07D 513/22

[52] U.S. Cl. .................................. 514/214; 540/494

[58] Field of Search .................. 260/239.3 P, 239.3 T; 514/214

[56] References Cited

U.S. PATENT DOCUMENTS 4,489,003 12/1984 Hunkeler et al. ........... 260/239.3 P

*Primary Examiner*—Robert T. Bond

*Attorney, Agent, or Firm*—Jon S. Saxe; Bernard S. Leon; Richard J. Mazza

[57] ABSTRACT

Compounds which are imidazodiazepine derivatives of the formula

I

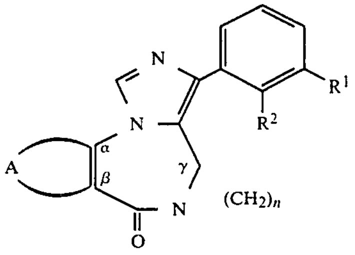

wherein A together with the carbon atoms denoted by $\alpha$ and $\beta$ signifies the group

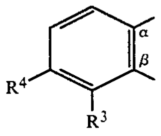

or

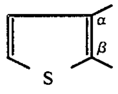

(a) (b)

one of $R^1$ and $R^2$ signifies hydrogen and the other signifies hydrogen, halogen or trifluoromethyl, $R^3$ and $R^4$ each signify hydrogen or halogen and n signifies the number 2 or 3, the compounds having the (S)- or (R,S)-configuration with reference to the carbon atom denoted by $\gamma$, and their pharmaceutically acceptable acid addition salts have been discovered which possess anxiolytic, anticonvulsant, muscle relaxant and sedative-hypnotic properties. They can be prepared into compositions, including pharmaceutically acceptable ones, using suitable inert carriers.

33 Claims, No Drawings

IMIDAZODIAZEPINE DERIVATIVES

SUMMARY OF THE INVENTION

The present invention is concerned with imidazodiazepine derivatives, and in particular, with imidazodiazepine derivatives of the general formula

I

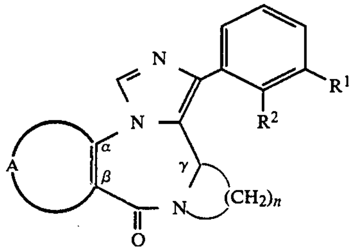

wherein A together with the carbon atoms denoted by $\alpha$ and $\beta$ signifies one of the groups

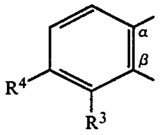

and

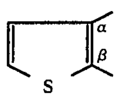

(a) (b)

one of $R^1$ and $R^2$ signifies hydrogen and the other signifies hydrogen, halogen or trifluoromethyl, $R^3$ and $R^4$ each signify hydrogen or halogen, and n signifies the number 2 or 3, the compounds having the (S)- or (R,S)-configuration with reference to the carbon atom denoted by $\gamma$, as well as pharmaceutically acceptable acid addition salts thereof.

These compounds are characterized by valuable pharmacodynamic properties.

Objects of the present invention are: compounds of formula I above and pharmaceutically acceptable acid addition salts thereof per se and as pharmaceutically active substances; the preparation of these compounds and salts; compositions, for example, medicaments, containing a compound of formula I or a pharmaceutically acceptable acid addition salt thereof; the preparation of such compositions; and the use of compounds of formula I and their pharmaceutically acceptable acid addition salts in the control of convulsions, anxiety states, muscle tensions, tension states and insomnia, or for the manufacture of medicaments, and especially medicaments having anticonvulsant, anxiolytic, muscle relaxant and sedative-hypnotic activity.

DETAILED DESCRIPTION OF THE INVENTION

The term "lower" denotes residues and compounds with at most 7, preferably at most 4, carbon atoms. The term "alkyl" denotes straight-chain or branched saturated hydrocarbon residues such as methyl, ethyl, n-propyl, isopropyl, n-butyl, s-butyl, t-butyl and the like. The term "aryl" denotes monocyclic aromatic hydrocarbon residues which can be substituted by lower alkyl, lower alkoxy, halogen, etc. The term "aralkyl" denotes an alkyl residue substituted by aryl in the sense of the previous definitions. The term "alkoxy" denotes alkyl groups attached via an oxygen atom such as methoxy, ethoxy, and the like. The terms "alkylthio" and "aralkylthio" denote alkyl or aralkyl groups, respectively, attached via a sulfur atom.

When the symbol A in formula I signifies the group (a), then preferably $R^3$ signifies halogen (especially chlorine or bromine) and $R^4$ signifies hydrogen. $R^1$ preferably signifies halogen (especially fluorine, chlorine or bromine) or trifluoromethyl, and $R^2$ preferably signifies hydrogen. The carbon atom denoted by $\gamma$ in formula I preferably has the (S)-configuration.

Preferred compounds of formula I in accordance with the invention are:

(S)-8-chloro-1-(m-chlorophenyl)-11,12,13,13a-tetrahydro-9H-imidazo[1,5-a]pyrrolo[2,1-c][1,4]benzodiazepin-9-one, (S)-8-chloro-1-(m-fluorophenyl)-11,12,13,13a-tetrahydro-9H-imidazo[1,5-a]pyrrolo[2,1-c][1,4]benzodiazepin-9-one and (S)-8-bromo-1-(m-chlorophenyl)-11,12,13,13a-tetrahydro-9H-imidazo[1,5-a]pyrrolo[2,1-c][1,4]benzodiazepin-9-one.

Further representative compounds of formula I are:

(S)-8-chloro-11,12,13,13a-tetrahydro-1-phenyl-9H-imidazo[1,5-a]pyrrolo[2,1-c][1,4]benzodiazepin-9-one, (S)-1-(m-chlorophenyl)-11,12,13,13a-tetrahydro-9H-imidazo[1,5-a]pyrrolo[2,1-c][1,4]benzodiazepin-9-one, (S)-8-chloro-1-(m-chlorophenyl)-7-fluoro-11,12,13,13a-tetrahydro-9H-imidazo[1,5-a]pyrrolo[2,1-c][1,4]benzodiazepin-9-one, (S)-8-chloro-11,12,13,13a-tetrahydro-1-($\alpha,\alpha,\alpha$-trifluoro-m-tolyl)-9H-imidazo[1,5-a]pyrrolo[2,1-c][1,4]benzodiazepin-9-one, (S)-1-(m-chlorophenyl)-7-fluoro-11,12,13,13a-tetrahydro-9H-imidazo[1,5-a]pyrrolo[2,1-c][1,4]benzodiazepin-9-one, (S)-1-(m-bromophenyl)-8-chloro-11,12,13,13a-tetrahydro-9H-imidazo[1,5-a]pyrrolo[2,1-c][1,4]benzodiazepin-9-one, (S)-1-(m-bromophenyl)-10,11,12,12a-tetrahydro-8H-imidazo[5,1-c]pyrrolo[1,2-a]thieno[3,2-e][1,4]diazepin-8-one, (S)-8-chloro-1-(m-chlorophenyl)-12,12a-dihydro-9H-azeto[2,1-c]imidazo[1,5-a][1,4]benzodiazepin-9-one and (S)-8-chloro-1-(o-chlorophenyl)-11,12,13,13a-tetrahydro-9H-imidazo[1,5-a]pyrrolo[2,1-c][1,4]benzodiazepin-9-one.

The compounds of formula I and their pharmaceutically acceptable acid addition salts can be prepared in accordance with the present invention by reacting a compound of the formula

II

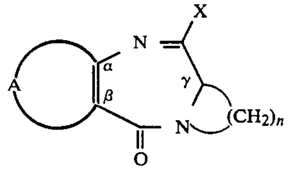

wherein A and n have the above significance and X signifies a leaving group, in the presence of a base, with an isonitrile of the formula

III

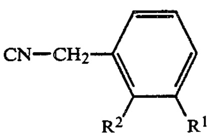

wherein $R^1$ and $R^2$ have the above significance, and, if desired, converting a compound of formula I thus obtained into a pharmaceutically acceptable acid addition salt.

In accordance with the present invention, compounds of formula I can, therefore, be manufactured from compounds of formula II and isocyanoacetic esters of formula III. The leaving group denoted by the symbol X in formula II is, for instance, a readily cleavable phosphinyl group, for example, a group of the formula $$-OP(O)(OR^5)_2 \text{ or } -OP(O)(NR^6R^7)_2$$

wherein $R^5$ signifies lower alkyl or aryl (such as phenyl) and $R^6$ and $R^7$ each signify lower alkyl, allyl, aryl (such as phenyl) or together with the nitrogen atom signify an unsubstituted or substituted heterocyclic ring with 3–8 members (such as morpholine), a halogen atom, a lower alkylthio group, a lower aralkylthio group, a lower N-nitrosoalkylamino group, a lower alkoxy group, a mercapto group, and the like (when X signifies a mercapto group, then the corresponding compound of formula II is the iminothiol form of the corresponding thiolactam). The reaction of the compounds of formula II and III is carried out in an inert solvent such as dimethylformamide, hexamethylphosphoric acid triamide, dimethyl sulphoxide, tetrahydrofuran, or any other suitable organic solvent, and in the presence of a base sufficiently strongly basic to form the anion of the isocyanoacetic ester of formula III. Suitable bases are alkali metal alkoxides such as sodium methoxide or potassium t-butoxide, alkali metal hydrides such as sodium hydride, alkali metal amides such as lithium amide or lithium diisopropylamide, tertiary amines such as triethylamine, and the like. The reaction temperature conveniently lies between about −40° C. and about room temperature (for example, 23°–25° C.).

If desired, compounds of formula I can be converted in accordance with the present invention into pharmaceutically acceptable acid addition salts. The preparation of such pharmaceutically acceptable acid addition salts is carried out according to usual methods. There come into consideration not only salts with inorganic acids, but also salts with organic acids, for example hydrochlorides, hydrobromides, sulfates, methanesulfonates, p-toluenesulfonates, oxalates, and the like.

The compounds of formula II and III used as starting materials are known or can be prepared by analogy to the known members of these classes of substances. The compounds of formula II are, as a rule, not isolated, but rather reacted in situ with the compounds of formula III.

The compounds of formula I have valuable pharmacodynamic properties and only low toxicity. They possess as a common characteristic a pronounced affinity to the central benzodiazepine receptors and have pronounced anxiolytic, anticonvulsant, muscle relaxant and sedative-hypnotic properties.

The affinity of compounds of formula I to the central benzodiazepine receptors has been determined according to the method described in Life Science 20, 2101–2110 (1977) and Science 198, 849–851 (1977). According to this method, the inhibition of the binding of tritiated diazepam at the specific benzodiazepine receptors in the cerebral cortex by the respective test substances is ascertained. The $IC_{50}$ ("50% inhibiting concentration") is that concentration of the respective test substance which brings about a 50 percent inhibition of the specific binding of the tritiated diazepam at the specific benzodiazepine receptors in the cerebral cortex.

The central properties of the compounds of formula I in accordance with the invention can be determined, for example, in the antipentetrazole test described hereinafter, which is generally recognized for recording anticonvulsant properties.

In this animal experiment, the compound under investigation is administered orally to female rats weighing 60–80 g and 30 minutes later there are administered i.p. 120 mg/kg of pentetrazole, which causes emprosthotonus and tonic stretchings of the fore and/or hind limbs in unprotected experimental animals 1–4 minutes after the injection. Ten experimental animals are used per dosage of test substance. After counting the protected experimental animals, the $ED_{50}$ is determined according to the Probit method. The $ED_{50}$ is that dosage which protects 50% of the experimental animals from the spasmodic seizures caused by pentetrazole.

The results obtained with representative members of the class of compounds defined by formula I in the experiments described previously are compiled in the following Table. Moreover, the Table contains data concerning the acute toxicity of some of these compounds ($LD_{50}$ in mg/kg in the case of single oral administration to mice).

| Compound | $IC_{50}$ in nM/l | Antipentetrazole test, $ED_{50}$ in mg/kg p.o | Toxicity $LD_{50}$ in mg/kg p.o. |
|---|---|---|---|
| A | 4.2 | 2.1 | 2500–5000 |
| B | 40 | 4.0 | 2500–5000 |
| C | 2.0 | 1.0 | >5000 |

A: (S)—8-Chloro-1-(m-chlorophenyl)-11,12,13,13a-tetrahydro-9H—imidazo[1,5-a]pyrrolo[2,1-c][1,4]benzodiazepin-9-one
B: (S)—8-Chloro-11,12,13,13a-tetrahydro-1-(α,α,α-trifluoro-m-tolyl)-9H—imidazo[1,5-a]pyrrolo[2,1-c][1,4]benzodiazepin-9-one
C: (S)—8-Bromo-1-(m-chlorophenyl)-11,12,13,13a-tetrahydro-9H—imidazo[1,5-a]pyrrolo[2,1-c][1,4]benzodiazepin-9-one The compounds of formula I and their pharmaceutically acceptable acid addition salts can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions. The administration can, however, also be carried out rectally, as in the form of suppositories, or parenterally, as in the form of injection solutions.

For the manufacture of pharmaceutical preparations, the products in accordance with the present invention can be processed with pharmaceutically inert, inorganic or organic carriers. As such carriers there can be used for tablets, coated tablets, dragees and hard gelatin capsules, for example, lactose, maize starch or derivatives thereof, talc, stearic acid or its salts, and the like. Suitable carriers for soft gelatin capsules are, for example, vegetable oils, waxes, fats, semi-solid and liquid polyols, and the like. Depending on the nature of the active substance, however, no carriers may be required in the case of soft gelatin capsules. Suitable carriers for the manufacture of solutions and syrups are, for example, water, polyols, saccharose, invert sugar, glucose, and the like. Suitable carriers for injection solutions are, for example, water, alcohols, polyols, glycerine, vegetable oils, and the like. Suitable carriers for suppositories are, for example, natural or hardened oils, waxes, fats, semi-liquid or liquid polyols, and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents, or antioxidants. They can also contain still other therepeutically valuable substances.

As mentioned earlier, medicaments containing a compound of formula I or a pharmaceutically acceptable acid addition salt thereof and a therapeutically inert excipient are also an object of the present invention, as is a process for the manufacture of such medicaments. This process comprises bringing one or more compounds of formula I or pharmaceutically acceptable acid addition salts thereof and, if desired, one or more other therapeutically valuable substances into a galenical administration from together with one or more therapeutically inert excipients.

As mentioned earlier, the compounds of formula I and their pharmaceutically acceptable acid addition salts can be used in the control or prevention of illnesses, and especially in the control of convulsions, anxiety states, muscle tensions, tension states and insomnia. The dosage can vary within wide limits and is, of course, fitted to the individual requirements in each particular case. In general, in the case of oral administration a daily dosage of about 1 mg to 100 mg comes into consideration.

The use of the compounds of formula I and their pharmaceutically acceptable acid addition salts for the manufacture of medicaments, especially medicaments having anxiolytic, anticonvulsant, muscle relaxant and sedative-hypnotic properties, is, as mentioned earlier, also an object of the invention.

DESCRIPTION OF THE SPECIFIC EMBODIMENTS

The following Examples are intended to illustrate the present invention in more detail, but are not intended to limit its extent in any manner. All temperatures are given in degrees Celsius.

EXAMPLE 1

A suspension of 9.57 g (38.2 mmol) of (S)-6-chloro-1,2,3,11a-tetrahydro-5H-pyrrolo[2,1-c][1,4]benzodiazepine-5,11(1OH)-dione in 25 ml of dry N,N-dimethylformamide is treated at −30° to −20° with 1.60 g (36.6 mmol) of sodium hydride (55 percent oil dispersion), the mixture is stirred at the above temperature for an additional 25 minutes, and then at −65° a solution of 9.75 g (36.3 mmol) of phosphoric acid diphenyl ester chloride in 8 ml of dry N,N-dimethylformamide is added dropwise. The mixture is stirred for 15 minutes in an acetone/dry-ice bath, and at −70° there is added a solution of 5.79 g (38.2 mmol) of 3-chlorobenzyl isocyanide in 4 ml of dry N,N-dimethylformamide and, subsequently, there is added at −70° to −45° a solution of 4.28 g (38.2 mmol) of potassium t-butylate in 10 ml of dry N,N-dimethylformamide. The mixture is allowed to warm to room temperature and neutralized with 2 ml of glacial acetic acid. The mixture is poured into 250 ml of water and extracted five times with methylene chloride. The combined organic extracts are washed three times with water, dried over magnesium sulfate, and evaporated. The crude product is chromatographed on silica gel while eluting with ethyl acetate and recrystallized from methylene chloride and ethyl acetate. There is obtained (S)-8-chloro-1-(m-chlorophenyl)-11,12,13,13a-tetrahydro-9H-imidazo[1,5-a]pyrrolo[2,1-c][1,4]benzodiazepin-9-one having a melting point of 244°–245°.

EXAMPLE 2

A suspension of 9.57 g (38.2 mmol) of (S)-6-chloro-1,2,3,11a-tetrahydro-5H-pyrrolo[2,1-c][1,4]benzodiazepine-5,11(1OH)-dione in 35 ml of dry N,N-dimethylformamide is treated at −30° to −20° with 1.60 g (36.6 mmol) of sodium hydride (55 percent oil dispersion), the mixture is stirred at the above temperature for a further 45 minutes, and then at −70° a solution of 9.75 g (36.3 mmol) of phosphoric acid diphenyl ester chloride in 8 ml of dry N,N-dimethylformamide is added dropwise. The mixture is stirred for an additional 45 minutes in an acetone/dry-ice bath, and at −70° to −60° there is added dropwise a solution of 4.44 g (37.9 mmol) of benzyl isocyanide in 5 ml of dry N,N-dimethylformamide, and subsequently there is added dropwise a solution of 4.28 g (38.2 mmol) of potassium t-butylate in 12 ml of dry N,N-dimethyl-formamide. The mixture is permitted to warm to room temperature and neutralized by the addition of 2 ml of glacial acetic acid. The mixture is poured into 250 ml of water and extracted five times with methylene chloride. The combined organic extracts are washed three times with water, dried over magnesium sulfate and evaporated. By chromatography of the residue on silica gel while eluting with ethyl acetate and subsequent recrystallization from ethyl acetate there is obtained (S)-8-chloro-11,12,13,13a-tetrahydro-1-phenyl-9H-imidazo[1,5-a]pyrrolo[2,1-c][1,4]benzodiazepin-9-one having a melting point of 233°–234°.

EXAMPLE 3

A suspension of 12.53 g (50 mmol) of (S)-6-chloro-1,2,3,11a-tetrahydro-5H-pyrrolo[2,1-c][1,4]benzodiazepine-5,11(1OH)-dione in 40 ml of dry N,N-dimethylformamide is treated at −30° to −20° with 2.18 g (50 mmol) of sodium hydride (55 percent oil dispersion), the mixture is stirred at the above temperature for an additional 45 minutes, and then at −65° there is added dropwise a solution of 13.43 g (50 mmol) of phosphoric acid diphenyl ester chloride in 8 ml of dry N,N-dimethylformamide. The mixture is stirred for 20 minutes in an acetone/dry-ice bath, and then at −70° there is added dropwise a solution of 6.80 g (50 mmol) of 3-fluorobenzyl isocyanide in 4 ml of dry N,N-dimethylformamide, and subsequently at −70° to −45° there is added dropwise a solution of 5.60 g (50 mmol) of potassium t-butylate in 10 ml of dry N,N-dimethylformamide. The mixture is allowed to warm to room temperature and treated with 2.5 ml of glacial acetic acid. The mixture is poured into 300 ml of water and extracted five times with methylene chloride. The combined organic extracts are washed three times with water, dried over magnesium sulfate, and evaporated. By chromatography of the residue on silica gel while eluting with ethyl acetate and subsequent recrystallization from ethyl acetate there is obtained (S)-8-chloro-1-(m-fluorophenyl)-11,12,13,13a-tetrahydro-9H-imidazo[1,5-a]pyrrolo[2,1- c][1,4]benzodiazepin-9-one having a melting point of 239°-240°.

EXAMPLE 4

A suspension of 6.49 g (30 mmol) of (S)-1,2,3,11a-tetrahydro-5H-pyrrolo[2,1-c][1,4]benzodiazepine-5,11(1OH)-dione in 30 mol of dry N,N-dimethylformamide is treated at −30° to −20° with 1.31 g (30 mmol) of sodium hydride (55 percent oil dispersion), the mixture is stirred at the above temperature for a further 35 minutes, and then at −65° there is added dropwise a solution of 8.06 g (30 mmol) of phosphoric acid diphenyl ester chloride in 6 ml of dry N,N-dimethylformamide. The mixture is left to warm to −40°, again cooled, and then at −70° there is added a solution of 4.55 g (30 mmol) of 3-chlorobenzyl isocyanide in 5 ml of dry N,N-dimethylformamide, and subsequently at −70° to −40° there is added a solution of 3.37 g (30 mmol) of potassium t-butylate in 7 ml of dry N,N-dimethylformamide. The mixture is left to warm to room temperature and neutralized by the addition of 1 ml of glacial acetic acid. The mixture is poured into 250 ml of water and extracted five times with methylene chloride. The combined organic extracts are washed three times with water, dried over magnesium sulfate, and evaporated. The residue is chromatographed on silica gel while eluting with ethyl acetate and recrystallized from ethyl acetate. There is obtained (S)-1-(m-chlorophenyl)-11,12,13,13a-tetrahydro-9H-imidazo[1,5-a]pyrrolo[2,1-c][1,4]benzodiazepin-9-one having melting point of 242°-243°.

EXAMPLE 5

A suspension of 9.40 g (35 mmol) of (S)-6-chloro-7-fluoro-1,2,3,11a-tetrahydro-5H-pyrrolo[2,1-c][1,4]-benzodiazepine-5,11(1OH)-dione in 40 ml of dry N,N-dimethylformamide is treated at −30° to −20° with 1.53 g (35 mmol) of sodium hydride (55 percent oil dispersion), the mixture is stirred at the above temperature for an additional 40 minutes, and then at −65° there is added dropwise a solution of 9.40 g (35 mmol) of phosphoric acid diphenyl ester chloride in 8 ml of dry N,N-dimethylformamide. The mixture is permitted to warm to −40°, again cooled, and at −65° there is added dropwise a solution of 5.03 g (35 mmol) of 3-chlorobenzyl isocyanide in 5 ml of dry N,N-dimethylformamide, and subsequently at −60° to −40° there is added dropwise a solution of 3.92 g (35 mmol) of potassium t-butylate in 10 ml of dry N,N-dimethylformamide. The mixture is left to warm to room temperature and neutralized with 2 ml of glacial acetic acid. The mixture is poured into 300 ml of water and extracted five times with methylene chloride. The combined organic extracts are washed three times with water, dried over magnesium sulphate and evaporated. The residue is chromatographed on silica gel while eluting with ethyl acetate and recrystallized from ethyl acetate. There is obtained (S)-8-chloro-1-(m-chlorophenyl)-7-fluoro-11,12,13,13a-tetrahydro-9H-imidazo[1,5-a]pyrrolo[2,1-c][1,4]benzodiazepin-9-one of melting point 238°-239°.

EXAMPLE 6

A suspension of 8.85 g (30 mmol) of (S)-6-bromo-1,2,3,11a-tetrahydro-5H-pyrrolo[2,1-c][1,4]benzodiazepine-5,11(1OH)-dione in 30 ml of dry N,N-dimethylformamide is treated at −30° to −20° with 1.31 g (30 mmol) of sodium hydride (55 percent oil dispersion), the mixture is stirred at the above temperature for a further 35 minutes, and then at −65° there is added dropwise a solution of 8.06 g (30 mmol) of phosphoric acid diphenyl ester chloride in 8 ml of dry N,N-dimethylformamide. The mixture is left to warm to −40°, again cooled, and at −65° there is added dropwise a solution of 4.55 g (30 mmol) of 3-chlorobenzyl isocyanide in 5 ml of dry N,N-dimethylformamide, and subsequently at −60° to −40° there is added dropwise a solution of 3.37 g (30 mmol) of potassium t-butylate in 7 ml of dry N,N-dimethylformamide. The mixture is left to warm to room temperature and neutralized by the addition of 2 ml of glacial acetic acid. The mixture is poured into 250 ml of water and extracted five times with methylene chloride. The combined organic extracts are washed three times with water, dried over magnesium sulfate, and evaporated. The residue is chromatographed on silica gel while eluting with ethyl acetate and recrystallized from ethyl acetate. There is obtained (S)-8-bromo-1-(m-chlorophenyl)-11,12,13,13a-tetrahydro-9H-imidazo[1,5-a]pyrrolo[2,1-c][1,4]benzodiazepin-9-one having a melting point of 238°-239°.

EXAMPLE 7

A suspension of 12.53 g (50 mmol) of (S)-6-chloro-1,2,3,11a-tetrahydro-5H-pyrrolo[2,1-c][1,4]benzodiazepine-5,11(1OH)-dione in 40 ml of dry N,N-dimethylformamide is treated at −30° to −20° with 2.18 g (50 mmol) of sodium hydride (55 percent oil dispersion), the mixture is stirred at the above temperature for a further 40 minutes, and then at −70° there is added dropwise a solution of 13.43 g (50 mmol) of phosphoric acid diphenyl ester chloride in 8 ml of dry N,N-dimethylformamide. The mixture is stirred for 20 minutes in an acetone/dry-ice bath, and then at −70° there is added dropwise a solution of 9.26 g (50 mmol) of 3-trifluoromethylbenzyl isocyanide in 7 ml of dry N,N-dimethylformamide and subsequently at −70° to −50° there is added dropwise a solution of 5.60 g (50 mmol) of potassium t-butylate in 10 ml of dry N,N-dimethylformamide. The mixture is allowed to warm to room temperature and neutralized with 2.5 ml of glacial acetic acid. The mixture is poured into 300 ml of water and extracted five times with methylene chloride. The combined organic extracts are washed three times with water, dried over magnesium sulfate, and evaporated. The residue is chromatographed on silica gel while eluting with ethyl acetate and recrystallized from ethyl acetate. There is obtained (S)-8-chloro-11,12,13,13a-tetrahydro-1-(α,α,α-trifluoro-m-tolyl)-9H-imidazo[1,5-a]pyrrolo[2,1-c][1,4]benzodiazepin-9-one having a melting point of 202°-204°.

EXAMPLE 8

A suspension of 8.20 g (35 mmol) of (S)-7-fluoro-1,2,3,11a-tetrahydro-5H-pyrrolo[2,1-c][1,4]benzodiazepine-5,11(10H)-dione in 40 ml of dry N,N-dimethylformamide is treated at −30° to −20° with 1.53 g (35 mmol) of sodium hydride (55 percent oil dispersion), the mixture is stirred at the above temperature for a further 35 minutes, and then at −60° there are added dropwise 7.25 ml (35 mmol) of phosphoric acid diphenyl ester chloride in 7 ml of dry N,N-dimethylformamide. The temperature is allowed to rise to −35°, the mixture is then again cooled to −70° and there is added a solution of 5.03 g (35 mmol) of 3-chlorobenzyl isocyanide in 5 ml of dry N,N-dimethylformamide, and subsequently there is added a solution of 3.92 g (35 mmol) of potassium t-butylate in 7 ml of dry N,N-dimethylformamide. After completion of the addition, the mixture is left to warm to 20°, neutralized by the addition of 1.5 ml of glacial acetic acid and poured into 250 ml of water. The mixture is extracted five times with methylene chloride, the combined organic extracts are washed three times with water, dried over magnesium sulfate, and evaporated. The residue is chromatographed on silica gel while eluting with ethyl acetate and recrystallized from ethyl acetate and n-hexane. There is obtained (S)-1-(m-chlorophenyl)-7-fluoro-11,12,13,13a-tetrahydro-9H-imidazo[1,5-a]pyrrolo[2,1-c][1,4]benzodiazepin-9-one having a melting point of 182°-183°.

EXAMPLE 9

10.03 g (40 mmol) of (S)-6-chloro-1,2,3,11a-tetrahydro-5H-pyrrolo[2,1-c][1,4]benzodiazepine-5,11(1O)-dione are suspended in 35 ml of dry N,N-dimethylformamide and treated at −30° to −20° with 1.75 g (40 mmol) of sodium hydride (55 percent oil dispersion). The mixture is stirred at −30° to −20° for a further 35 minutes, there is subsequently added dropwise at −60° a solution of 8.3 ml (40 mmol) of phosphoric acid diphenyl ester chloride in 8 ml of dry N,N-dimethylformamide, and the mixture is left to warm to −35°. The mixture is again cooled to −70° and there is added a solution of 7.80 g (40 mmol) of 3-bromobenzyl isocyanide in 4 ml of dry N,N-dimethylformamide, and there is subsequently added a solution of 4.50 g (40 mmol) of potassium t-butylate in 10 ml of dry N,N-dimethylformamide. After completion of the addition, the mixture is left to warm to 20°, neutralized with 1 ml of glacial acetic acid and poured into 250 ml of water. The mixture is extracted five times with methylene chloride, the combined organic extracts are washed three times with water, dried over magnesium sulfate, and evaporated. The residue is chromatographed on silica gel while eluting with ethyl acetate and subsequently recrystallized from ethyl acetate. There is obtained (S)-1-(m-bromophenyl)-8-chloro-11,12,13,13a-tetrahydro-9H-imidazo[1,5-a]pyrrolo[2,1-c][1,4]benzodiazepin-9-one having a melting point of 247°-248°.

EXAMPLE 10

A suspension of 8.17 g (36.8 mmol) of (S)-5a,6,7,8a-tetrahydro-5H-pyrrolo[1,2-a]thieno[3,2-e][1,4]diazepine-5,10(4H)-dione in 35 ml of dry N,N-dimethylformamide is treated at −30° to −20° with 1.60 g (36.8 mmol) of sodium hydride (55 percent oil dispersion), the mixture is stirred at the above temperature for 45 minutes, and then at −70° there is added dropwise a solution of 9.90 g (36.8 mmol) of phosphoric acid diphenyl ester chloride in 7 ml of dry N,N-dimethylformamide. The mixture is allowed to warm to −40°, again cooled, and at −70° there is added a solution of 7.21 g (36.8 mmol) of 3-bromobenzyl isocyanide in 4 ml of dry N,N-dimethylformamide, and subsequently at −70° to −40° there is added a solution of 4.13 g (36.8 mmol) of potassium t-butylate in 10 ml of dry N,N-dimethylformamide. The mixture is left to warm to room temperature and neutralized by the addition of 2 ml of glacial acetic acid. The mixture is poured into 400 ml of water and extracted four times with methylene chloride. The organic extracts are washed four times with water, dried over magnesium sulfate, and evaporated. The residue is chromatographed on silica gel while eluting with ethyl acetate and subsequently recrystallized from ethyl acetate and hexane. There is obtained (S)-1-(m-bromophenyl)-10,11,12,12a-tetrahydro-8H-imidazo[5,1-c]pyrrolo[1,2-a]thieno[3,2-e][1,4]diazepin-8-one having a melting point of 169°-170°.

EXAMPLE 11

A suspension of 11.83 g (50 mmol) of (S)-5-chloro-1,10a-dihydro-azeto[2,1-c][1,4]benzodiazepine-4,10-(2H,9H)-dione in 35 ml of dry N,N-dimethylformamide is treated at −30° to −20° with 2.18 g (50 mmol) of sodium hydride (55 percent oil dispersion), the mixture is stirred at the above temperature for a further 35 minutes, and then at −70° there is added dropwise a solution of 13.43 g (50 mmol) of phosphoric acid diphenyl ester chloride in 8 ml of dry N,N-dimethylformamide. After stirring for 20 minutes in an acetone/dry-ice bath there is added dropwise at −70° a solution of 7.58 g (50 mmol) of 3-chlorobenzyl isocyanide in 4 ml of dry N,N-dimethylformamide, and subsequently at −65° to −40° there is added dropwise a solution of 5.61 g (50 mmol) of potassium t-butylate in 9 ml of dry N,N-dimethylformamide. The mixture is left to warm to room temperature and neutralized by the addition of 2.5 ml of glacial acetic acid. The mixture is poured into 300 ml of water and extracted five times with methylene chloride. The combined organic extracts are washed three times with water, dried over magnesium sulfate, and concentrated. The residue is chromatographed on silica gel while eluting with ethyl acetate and recrystallized twice from ethyl acetate. There is obtained (S)-8-chloro-1-(m-chlorophenyl)-12,12a-dihydro-9H-azeto[2,1-c]imidazo[1,5-a][1,4]benzodiazepin-9-one having a melting point of 221°-223°.

EXAMPLE 12

A suspension of 12.53 g (50 mmol) of (S)-6-chloro-1,2,3,11a-tetrahydro-5H-pyrrolo[2,1-c][1,4]benzodiazepine-5,11(1OH)-dione in 50 ml of dry N,N-dimethylformamide is treated at −30° to −20° with 2.07 g (47.5 mmol) of sodium hydride (55 percent oil dispersion), the mixture is stirred at the above temperature for a further 30 minutes, and then at −65° there is added dropwise a solution of 12.89 g (48 mmol) of phosphoric acid diphenyl ester chloride in 6 ml of dry N,N-dimethylformamide. The mixture is stirred for 20 minutes in an acetone/dry-ice bath, and then at −70° there is added a solution of 7.58 g (50 mmol) of 2-chlorobenzyl isocyanide in 5 ml of dry N,N-dimethylformamide, and subsequently at −70° to −40° there is added a solution of 5.61 g (50 mmol) of potassium t-butylate in 10 ml of dry N,N-dimethylformamide. The mixture is left to warm to room temperature and neutralized with 2 ml of glacial acetic acid. The mixture is poured into 300 ml of water and extracted five times with methylene chloride. The combined organic extracts are washed three times with water, dried over magnesium sulfate, and evaporated. By chromatography of the residue on silica gel while eluting with ethyl acetate and subsequent recrystallization from ethyl acetate and n-hexane there is obtained (S)-8-chloro-1-(o-chlorophenyl)-11,12,13,13a-tetrahydro-9H-imidazo[1,5-a]pyrrolo[2,1-c][1,4]benzodiazepin-9-one having a melting point of 246°-247°.

Compounds of formula I defined earlier, such as (S)-8-chloro-1-(m-chlorophenyl)-11,12,13,13a-tetrahydro-9H-imidazo[1,5-a]pyrrolo[2,1-c][1,4]benzodiazepin-9-one, can be used as active substances for the manufacture of pharmaceutical preparations as indicated in Example A hereinafter.

EXAMPLE A

Tablets of the following composition are manufactured in the usual manner:

| | mg/tablet |
|---|---|
| Active substance | 5 |
| Lactose | 140 |
| Maize starch | 46 |
| Polyvinylpyrrolidine | 8 |
| Magnesium stearate | 1 |
| Tablet weight | 200 |

We claim:

1. A compound of the formula

I

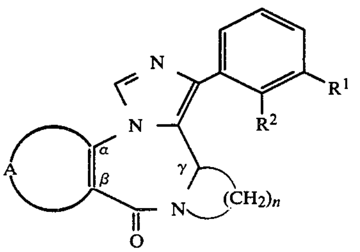

wherein A together with the carbon atoms denoted by $\alpha$ and $\beta$ represents one of the groups

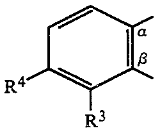

and

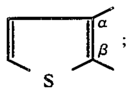

;

(a) (b)

one of $R^1$ and $R^2$ represents hydrogen and the other represents hydrogen, halogen or trifluoromethyl; $R^3$ and $R^4$ each represent hydrogen or halogen; and n is 2 or 3, the compound having the (S)- or (R,S)-configuration with reference to the carbon atom denoted by $\gamma$, and pharmaceutically acceptable acid addition salts thereof.

2. A compound according to claim 1, wherein A represents the group (a), $R^3$ represents halogen, and $R^4$ represents hydrogen.

3. A compound according to claim 2, wherein $R^3$ is chlorine.

4. A compound according to claim 2, wherein $R^3$ is bromine.

5. A compound according to claim 1, wherein $R^1$ repesents trifluoromethyl and $R^2$ represents hydrogen.

6. A compound according to claim 1, wherein $R^1$ represents halogen and $R^2$ represents hydrogen.

7. A compound according to claim 6, wherein $R^1$ represents a member selected from the group consisting of fluorine, chlorine and bromine.

8. A compound according to claim 1, wherein the carbon atom denoted by $\gamma$ has the (S)-configuration.

9. (S)-8-chloro-1-(m-chlorophenyl)-11,12,13,13a-tetrahydro-9H-imidazo[1,5-a]pyrrolo[2,1-c][1,4]benzodiazepin-9-one.

10. (S)-8-chloro-1-(m-fluorophenyl)-11,12,13,13a-tetrahydro-9H-imidazo[1,5-a]pyrrolo[2,1-c][1,4]benzodiazepin-9-one.

11. (S)-8-bromo-1-(m-chlorophenyl)-11,12,13,13a-tetrahydro-9H-imidazo[1,5-a]pyrrolo[2,1-c][1,4]benzodiazepin-9-one.

12. (S)-8-chloro-11,12,13,13a-tetrahydro-1-phenyl-9H-imidazo[1,5-a]pyrrolo[2,1-c][1,4]benzodiazepin-9-one.

13. (S)-1-(m-chlorophenyl)-11,12,13,13a-tetrahydro-9H-imidazo[1,5-a]pyrrolo[2,1-c][1,4]benzodiazepin-9-one.

14. (S)-8-chloro-1-(m-chlorophenyl)-7-fluoro-11,12,13,13a-tetrahydro-9H-imidazo[1,5-a]pyrrolo[2,1-c][1,4]benzodiazepin-9-one.

15. (S)-8-chloro-11,12,13,13a-tetrahydro-1-($\alpha,\alpha,\alpha$-trifluoro-m-tolyl)-9H-imidazo[1,5-a]pyrrolo[2,1-c][1,4]-benzodiazepin-9-one.

16. (S)-1-(m-chlorophenyl)-7-fluoro-11,12,13,13a-tetrahydro-9H-imidazo[1,5-a]pyrrolo[2,1-c][1,4]benzodiazepin-9-one.

17. (S)-1-(m-bromophenyl)-8-chloro-11,12,13,13a-tetrahydro-9H-imidazo[1,5-a]pyrrolo[2,1-c][1,4]benzodiazepin-9-one.

18. (S)-1-(m-bromophenyl)-10,11,12,12a-tetrahydro-8H-imidazo[5,1-c]pyrrolo[1,2-a]thieno[3,2-e][1,4]diazepin-8-one.

19. (S)-8-chloro-1-(m-chlorophenyl)-12,12a-dihydro-9H-aceto[2,1-c]imidazo[1,5-a][1,4]benzodiazepin-9-one.

20. (S)-8-chloro-1-(o-chlorophenyl)-11,12,13,13a-tetrahydro-H-imidazo[1,5-a]pyrrolo[2,1-c][1,4]benzodiazepin-9-one.

21. An anxiolytic, anticonvulsant, muscle relaxant and sedative-hypnotic composition which comprises (1) an effective amount of a compound of the formula

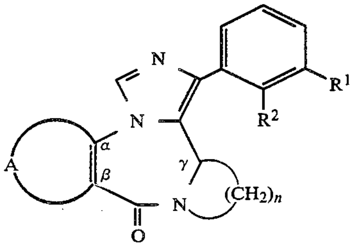

wherein A together with the carbon atoms denoted by $\alpha$ and $\phi$ represents one of the groups

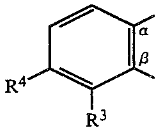

and

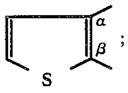

;

(a) (b)

one of $R^1$ and $R^2$ represents hydrogen and the other represents hydrogen, halogen or trifluoromethyl; $R^3$ and $R^4$ each represent hydrogen or halogen; and n is 2 or 3, the compound having the (S)- or (R,S)-configuration with reference to the carbon atom denoted by $\gamma$, or a pharmaceutically acceptable acid addition salt thereof, and (2) an inert carrier.

22. A composition according to claim 21, wherein A represents the group (a), $R^3$ represents halogen, and $R^4$ represents hydrogen.

23. A composition according to claim 22, wherein $R^3$ is chlorine.

24. A composition according to claim 22, wherein $R^3$ is bromine.

25. A composition according to claim 21, wherein $R^1$ represents halogen and $R^2$ represents hydrogen.

26. A composition according to claim 25, wherein $R^1$ represents a member selected from the group consisting of fluorine, chlorine, and bromine.

27. A composition according to claim 21, wherein $R^1$ represents trifluoromethyl and $R^2$ represents hydrogen.

28. A composition according to claim 1, wherein the carbon atom denoted by $\gamma$ has the (S)-configuration.

29. A composition according to claim 21, wherein the compound is (S)-8-chloro-1-(m-chlorophenyl)-11,12,13,13a-tetrahydro-9H-imidazo[1,5-a]pyrrolo[2,1-c][1,4]benzodiazepin-9-one.

30. A composition according to claim 21, wherein the compound is (S)-8-chloro-1-(m-fluorophenyl)-11,12,13,13a-tetrahydro-9H-imidazo[1,5-a]pyrrolo[2,1-c][1,4]benzodiazepin-9-one.

31. A composition according to claim 21, wherein the compound is (S)-8-bromo-1-(m-chlorophenyl)-11,12,13,13a-tetrahydro-9H-imidazo[1,5-a]pyrrolo[2,1-c][1,4]benzodiazepin-9-one.

32. A composition according to claim 21, wherein the compound is selected from the group consisting of:

(S)-8-chloro-11,12,13,13a-tetrahydro-1-phenyl-9H-imidazo[1,5-a]pyrrolo[2,1-c][1,4]benzodiazepin-9-one, (S)-1-(m-chlorophenyl)-11,12,13,13a-tetrahydro-9H-imidazo[1,5-a]pyrrolo[2,1-c][1,4]benzodiazepin-9-one, (S)-8-chloro-1-(m-chlorophenyl)-7-fluoro-11,12,13,13a-tetrahydro-9H-imidazo[1,5-a]pyrrolo[2,1-c][1,4]benzodiazepin-9-one, (S)-8-chloro-11,12,13,13a-tetrahydro-1-($\alpha$,$\alpha$,$\alpha$-trifluoro-m-tolyl)-9H-imidazo[1,5-a]pyrrolo[2,1-c][1,4]-benzodiazepin-9-one, (S)-1-(m-chlorophenyl)-7-fluoro-11,12,13,13a-tetrahydro-9H-imidazo[1,5-a]pyrrolo[2,1-c][1,4]benzodiazepin-9-one, (S)-1-(m-bromophenyl)-8-chloro-11,12,13,13a-tetrahydro-9H-imidazo[1,5-a]pyrrolo[2,1-c][1,4]benzodiazepin-9-one, (S)-1-(m-bromophenyl)-10,11,12,12a-tetrahydro-8H-imidazo[5,1-c]pyrrolo[1,2-a]thieno[3,2-e][1,4]diazepin-8-one, (S)-8-chloro-1-(m-chlorophenyl)-12,12a-dihydro-9H-azeto[2,1-c]imidazo[1,5-a][1,4]benzodiazepin-9-one, and (S)-8-chloro-1-(o-chlorophenyl)-11,12,13,13a-tetrahydro-9H-imidazo[1,5-a]pyrrolo[2,1-c][1,4]benzodiazepin-9-one.

33. A composition according to claim 21, in which the carrier is a therapeutically inert excipient.

* * * * *